United States Patent [19]

Albertsson et al.

[11] 4,302,677
[45] Nov. 24, 1981

[54] CONTROL ARRANGEMENT FOR FLUID STERILIZING APPARATUS

[76] Inventors: Nils L. Albertsson, Grevgatan 42, S-114 53 Stockholm; Tor A. Albertsson, Akerbyvägen 88, S-183 35 Täby; Lennart R. Nordell, Orrspelsvägen 12, S-182 75 Stocksund; Björn V. B. Björk, Vinterstigen 20, S-150 24 Rönninge; Refaat M. El-Sayed, Näsbydalsvägen 14, S-183 31 Täby, all of Sweden

[21] Appl. No.: 133,971

[22] Filed: Mar. 26, 1980

[30] Foreign Application Priority Data

Mar. 27, 1979 [SE] Sweden .............................. 7902704
Jan. 4, 1980 [SE] Sweden .............................. 8000062

[51] Int. Cl.³ ........................................... G01N 21/01
[52] U.S. Cl. ................................ 250/429; 250/432 R
[58] Field of Search ............... 250/428, 429, 430, 431, 250/432 R, 436, 372

[56] References Cited

U.S. PATENT DOCUMENTS

| | | | |
|---|---|---|---|
| 3,413,465 | 11/1968 | Harrison et al. | 250/430 |
| 3,456,107 | 7/1969 | Robertson | 250/436 |
| 3,471,693 | 10/1969 | Veloz | 250/431 |
| 3,562,520 | 2/1971 | Hippen | 250/432 |
| 3,566,105 | 2/1971 | Wiltrout et al. | 250/430 |

*Primary Examiner*—Bruce C. Anderson
*Attorney, Agent, or Firm*—Alfred E. Miller

[57] ABSTRACT

A sterilizing apparatus for liquid, preferably water, in which the liquid passes through a sterilizing chamber only when the apparatus has sufficient sterilizing capability. The apparatus is provided within ultraviolet-light source, a heat sensing means, and a light intensity sensing means, the latter two means being connected to a valve controlling the flow of liquid through the apparatus. A filter is also provided through which the liquid passes before it reaches the light source.

5 Claims, 2 Drawing Figures

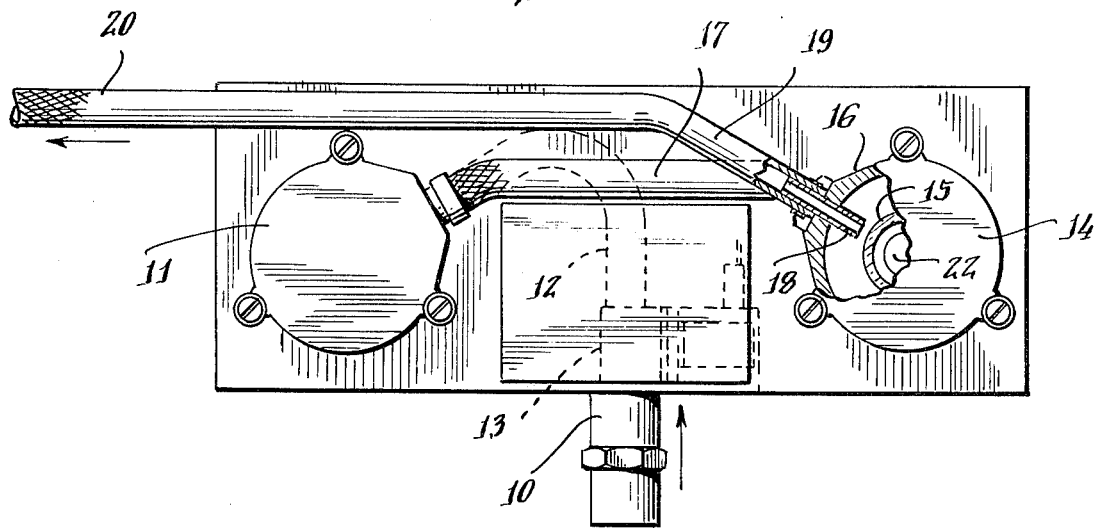
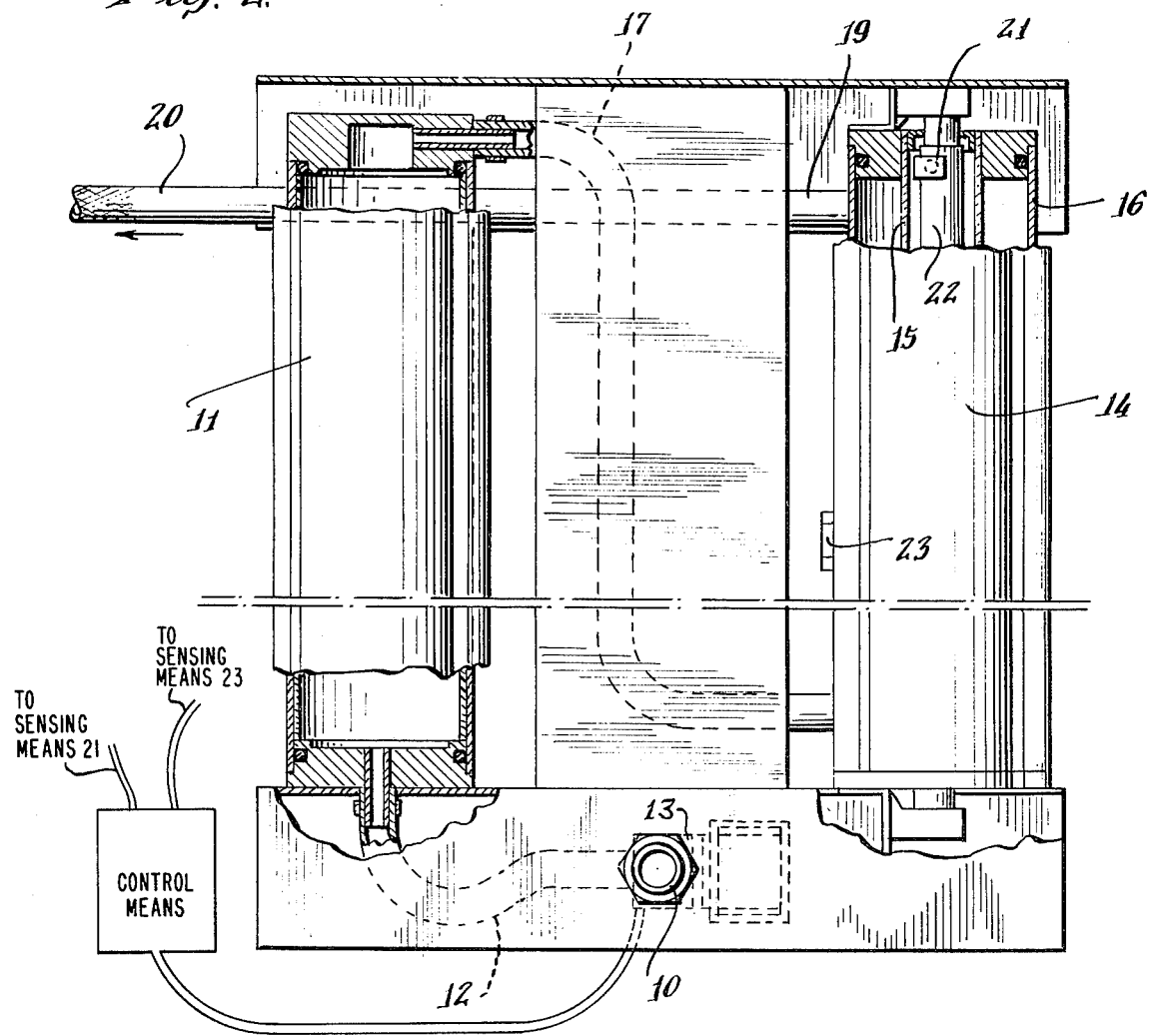

CONTROL ARRANGEMENT FOR FLUID STERILIZING APPARATUS

BACKGROUND OF THE INVENTION

Sterilizing apparatus, for example for the purification of water, are known in which purification is achieved by means of one or more ultraviolet radiation sources mounted in a large cylinder which are surrounded by cylindrical protecting tubes. The water to be purified is circulated through the large cylinder and between the protecting tubes. This known apparatus, for instance, is disclosed in U.S. Pat. Nos. 3,456,107, 3,462,597, 3,562,520 and 3,566,105, respectively.

It is extremely important that sterilizing apparatus of the type described work in a satisfactory manner, i.e. with sufficient capacity of purification. However, should for some reason this capacity decrease so that the quality of the discharged water cannot be guaranteed, the apparatus must automatically be switched off, so that water in which bacteria killing is unsatisfactory must not be allowed to pass through the unit.

Furthermore, it is very important that the liquid which is to be exposed to ultraviolet light is clear and free from suspended particles, because the transmission ability of the ultraviolet light decreases considerably if the liquid is cloudy. Therefore, the apparatus also comprises a filter having a readily exchangeable filter cartridge through which the liquid passes before reaching the chamber in which it is exposed to ultraviolet light.

Some disadvantages of the apparatus as shown and described in the above U.S. patents are that they are expensive because they include complicated sensor systems for detecting the intensity and the wave length of the ultraviolet light, as well as complicated cleaning systems for the glass in the apparatus which is irradiated by the ultraviolet light, and becomes soiled and dirty because of insufficient cleaning of incoming water or other type of liquid.

This invention relates to a sterilizing apparatus for liquid, preferably water, and having a light source emitting ultraviolet radiation. The light source is arranged to emit radiation through a chamber through which a liquid passes to be sterilized, with the liquid, prior to flowing through the chamber, passing through a filter.

An object of the present invention is to provide a sterilizing apparatus which is controlled by simple components and is safe and reliable in operation, easy to install, and can be manufactured at a price which permits widespread use in countries having water supply problems.

In order that the invention will be more clearly understood, it will now be disclosed in greater detail with reference to the accompanying drawings, in which:

FIG. 1 is a plan view of an apparatus according to the invention; and

FIG. 2 is a front elevational view, partly in section of the apparatus, with parts of its cover removed for purposes of clarity.

DESCRIPTION OF THE PREFERRED EMBODIMENT

In FIG. 1, in which an upper hood is assumed to be removed so that the main parts of the apparatus can be seen, there is an inlet 10 for water, a filter 11 for the feed water, which through a pipe 12 is conducted to the filter 11 after having passed a reducing unit, and a magnetic valve 13, and possibly also a pressure switch.

The filter 11 comprises a filter cartridge, which is easy to exchange, and has several components, and thus also several functions. The filter comprises (a) an anion exchanger of cellulose matrix, which takes up humic acid and high-molecular weight anions, such as anionic detergents, dyes and organic phosphorous compounds, (b) a cation exchanger of zeolite matrix for removing ammonia, (c) an active carbon unit, comprising two types of GAC-particles for removing various high and low molecular weight organic compounds. The filter cartridge can be provided with further components for filtration of water having specific contaminations, but the above-mentioned composition will probably be adequate in most applications.

As seen in FIG. 2, a double-wall container 14 whose inner wall 15 is made of quartz glass and surrounds a light source for ultraviolet radiation, and whose outer wall 16 is made of anodized extruded aluminium. Aluminium has been chosen because of its extremely high reflectivity for ultraviolet light within the bacteria killing area. Thus, this choice of material increases the killing capability considerably. Water passing through the filter 11 is moved through a pipe 17, and conducted to the lower part of the container 14 and passes through the chamber, between the walls 15 and 16, while being exposed to the ultraviolet radiation, and thereafter to an outlet 18 in the upper part of the container 14, from which the sterilized water is conducted through a pipe 19 to the outlet 20 of the apparatus.

In FIG. 2 details from FIG. 1 are shown which bear the same reference numerals as in FIG. 1. Also, a heat sensing means 21, such as a thermistor, is shown diagrammatically and arranged adjacent to the light source 22; and a light intensity sensing means 23, such as a photo diode, is arranged at a given distance from the light source 22, i.e. in the outer wall 16 of the container 14.

As seen in FIG. 1, the distance between the outer end of the outlet 18 and the inner wall 15, and hence the light source 22, is considerably less than the distance between the inner wall 15, and hence the light source 22, and the light intensity sensing means 23. Since both the incoming liquid and the outgoing liquid to and from the light chamber, flow through connections situated very near the light source, a high radiation dose can be guaranteed both at the inlet and at the outlet.

The pipe 17 for feeding water from the filter 11 to the container 14 opens into an inlet which is of the same shape as and placed directly under the outlet 18. Thus, the distance between this inlet to the chamber and the light source is about the same as the distance between the outlet 18 in the chamber and the light source.

The heat sensing means 21 and the light intensity sensing means 23 are at their respective outside locations and connected to an inlet side of the magnetic valve 13 for controlling purpose and the two means are so dimensional and adjusted that water passes through the sterilization chamber only when the light source has sufficient sterilizing capability, i.e. when its temperature and the light intensity passing therethrough, at least have reached given minimum levels, which are predetermined. The principal purpose of the present invention is, above all, to ensure that the light source always works within the right temperature interval with the aid of a thermistor, that is, in the interval in which the source surely emits about 90% of its light with bacteria killing capability. Consequently, outside of the above-described interval, the light source does not uniformly and regularly emit light of a suitable wave length. If the light source does not work within the right temperature interval, the temperature sensing means, i.e. the thermistor, will automatically switch off the supply of feed water.

It should be evident that, it is not necessary to use a complicated and expensive light intensity sensing means, which particularly measures the bacteria killing wave length, but rather an inexpensive means, such as a photo-transistor, which is preferably used. The foregoing arrangement also permits the possibility of creating a sensor system with simple and inexpensive components, and which is fully safe.

When the present apparatus is started up by switching on its main switch, a time circuit in the electronic unit is also started. The object of providing a time circuit is to prevent the manipulation of the magnetic valve before the light source has reached its full working capacity. When the time for the time circuit has been completed, one of the criteria is fulfilled in that the apparatus will produce sterilized water. Further criteria, as previously disclosed hereinabove, are that the temperature and the intensity of the light source reach given levels that are predetermined. If not, the magnetic valve will close the water inlet, thereby preventing water from entering the apparatus.

The electronic unit is also provided with means for disconnecting the apparatus under abnormal circumstances, for example, if the temperature of the light source should become extremely high, and if the water pressure should become excessive, etc.

While one embodiment of the present invention has been disclosed and described, it will be apparent that variations and modifications may be made therein without departing from the spirit and scope of the invention as defined in the following claims.

What is claimed is:

1. A control arrangement for fluid sterilizing apparatus provided with a light source being arranged to emit ultraviolet radiation through a chamber passed through by the liquid to be sterilized that has passed through a filter prior to entering said chamber comprising: a thermistor heat sensing means positioned adjacent to said light source, and and a photo thermistor light intensity sensing means for said light source being located at a predetermined distance from said light source, and a control means into which the respective outputs of each of said sensing means is connected, said control means having a valve whose input receives the aforementioned outputs to regulate the flow of liquid through said chamber, said two sensing means being so dimensioned and adjusted that liquid passes through said chamber only when the light source has sufficient sterilizing capability.

2. An arrangement as claimed in claim 1 wherein said predetermined distance is at least as great as the greatest of the distances between an inlet to the chamber for liquid and said light source respectively and between an outlet in the chamber for liquid and said light source.

3. The arrangement as claimed in claim 1 wherein said chamber is a double-walled cylindrical container having said light source mounted concentrically and approximately in the middle thereof, said inner cylindrical wall surrounding said light source being glass, the distance between said inlet to said chamber and the light source being approximately the same as the distance between said outlet of said chamber and said light source, and considerably less than the distance between the light source and said light intensity sensing means.

4. A control arrangement as claimed in claim 3 wherein said cylindrical container is preferably constituted of anodized aluminum.

5. A control arrangement as claimed in claim 1 wherein said filter comprises an anion exchanger, a cation exchanger, and an active carbon unit.

* * * * *